United States Patent
Tsipouras et al.

(10) Patent No.: US 7,196,788 B2
(45) Date of Patent: Mar. 27, 2007

(54) DEVICE AND METHOD FOR DETECTING AND LOCALIZING CELLS BY MEANS OF PHOTOSENSITIVE WAVEGUIDES

(75) Inventors: Petros Tsipouras, Madison, CT (US); Trianaflyllos Tafas, Rocky Hill, CT (US)

(73) Assignee: Ikonisys, Inc., New Haven, CT (US)

( * ) Notice: Subject to any disclaimer, the term of this patent is extended or adjusted under 35 U.S.C. 154(b) by 0 days.

(21) Appl. No.: 10/868,712

(22) Filed: Jun. 15, 2004

(65) Prior Publication Data

US 2004/0223151 A1 Nov. 11, 2004

Related U.S. Application Data

(63) Continuation of application No. 10/182,210, filed on Jul. 22, 2002, now Pat. No. 6,759,663.

(51) Int. Cl.
*G01N 21/64* (2006.01)

(52) U.S. Cl. .............. 356/317; 250/458.1; 385/12

(58) Field of Classification Search .......... 356/317, 356/318, 417; 250/458.1, 459.1, 461.1, 461.2, 250/227.14; 422/82.06, 82.07, 82.11; 436/172; 385/5, 12, 122
See application file for complete search history.

(56) References Cited

U.S. PATENT DOCUMENTS

| | | | |
|---|---|---|---|
| 4,746,179 A | 5/1988 | Dahne et al. | |
| 5,166,515 A | 11/1992 | Attridge | |
| 5,691,205 A | 11/1997 | Kawabata et al. | |
| 5,809,185 A * | 9/1998 | Mitchell | 385/12 |
| 6,759,663 B2 * | 7/2004 | Tsipouras et al. | 250/458.1 |
| 2002/0191182 A1 | 12/2002 | Tsipouras et al. | |
| 2004/0223151 A1 | 11/2004 | Petros et al. | |

FOREIGN PATENT DOCUMENTS

| | | |
|---|---|---|
| DE | 27 24 748 A1 | 12/1978 |
| JP | 63 273042 A | 11/1988 |
| WO | WO-01/53809 A1 | 7/2001 |

OTHER PUBLICATIONS

Dorf ed., 1997, The Electrical Engineering Handbook Second Edition, CRC Press, Boca Raton, Fl. chap. 42 pp. 1069-1095.
Moerner et al. Polymeric Photorefractive Materials, Chemical Reviews, 1994 vol. 19 pp. 127-156.
Bolink Henk et al. 1993 SPIE proc. vol. 2025B: pp. 292-297.

* cited by examiner

*Primary Examiner*—F. L. Evans
(74) *Attorney, Agent, or Firm*—Kelley Drye & Warren LLP

(57) ABSTRACT

The present invention provides devices and methods for detection of particles, such as biological cells, in samples using a photosensitive waveguide. The photosensitive waveguide changes its transmissivity in a detectable manner in response to controlling radiation emitted from the particles. In preferred embodiments, the waveguide is two-dimensional and the position of the particles as well as their presence is obtained by scanning the waveguide in two non-parallel directions. The provided devices are preferably used to locate labeled cells. The present invention also includes control systems and methods for detecting and locating cells using the devices provided.

17 Claims, 7 Drawing Sheets

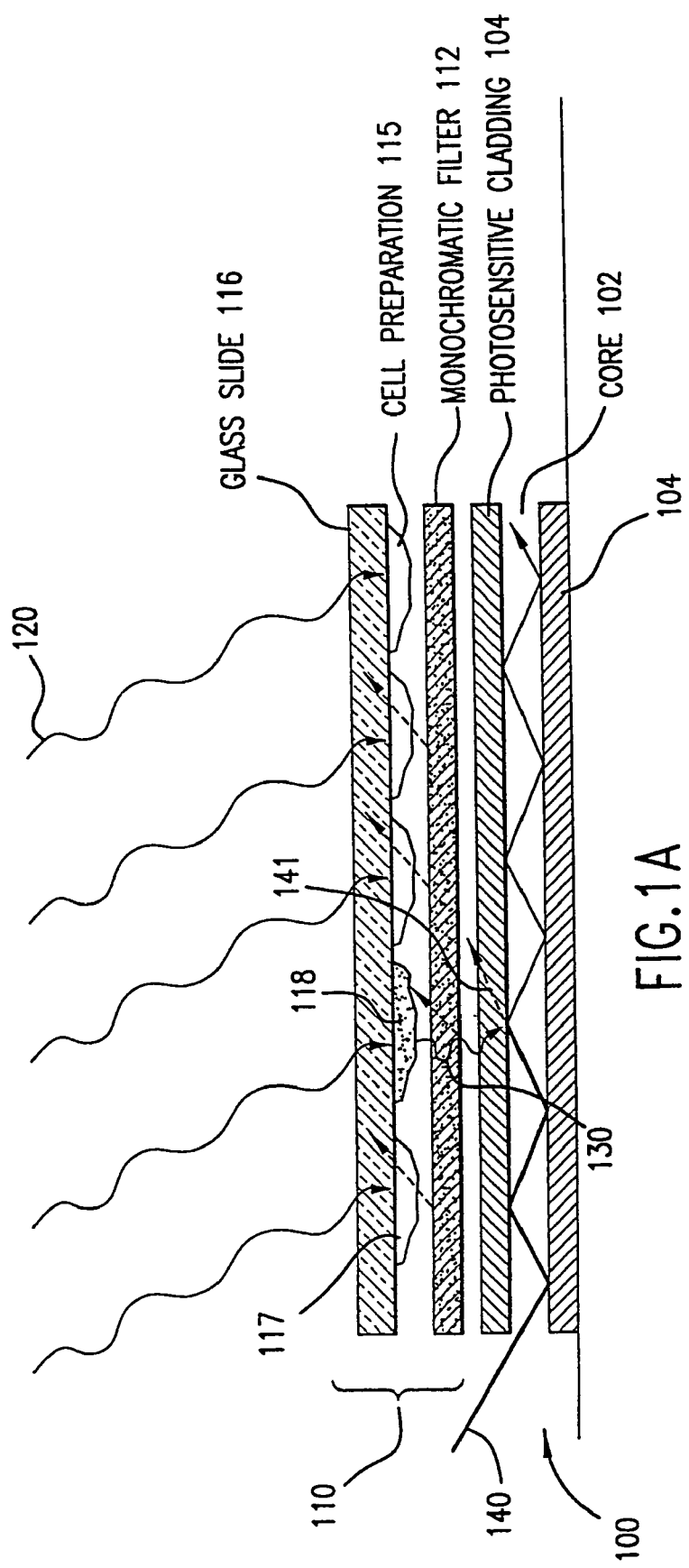

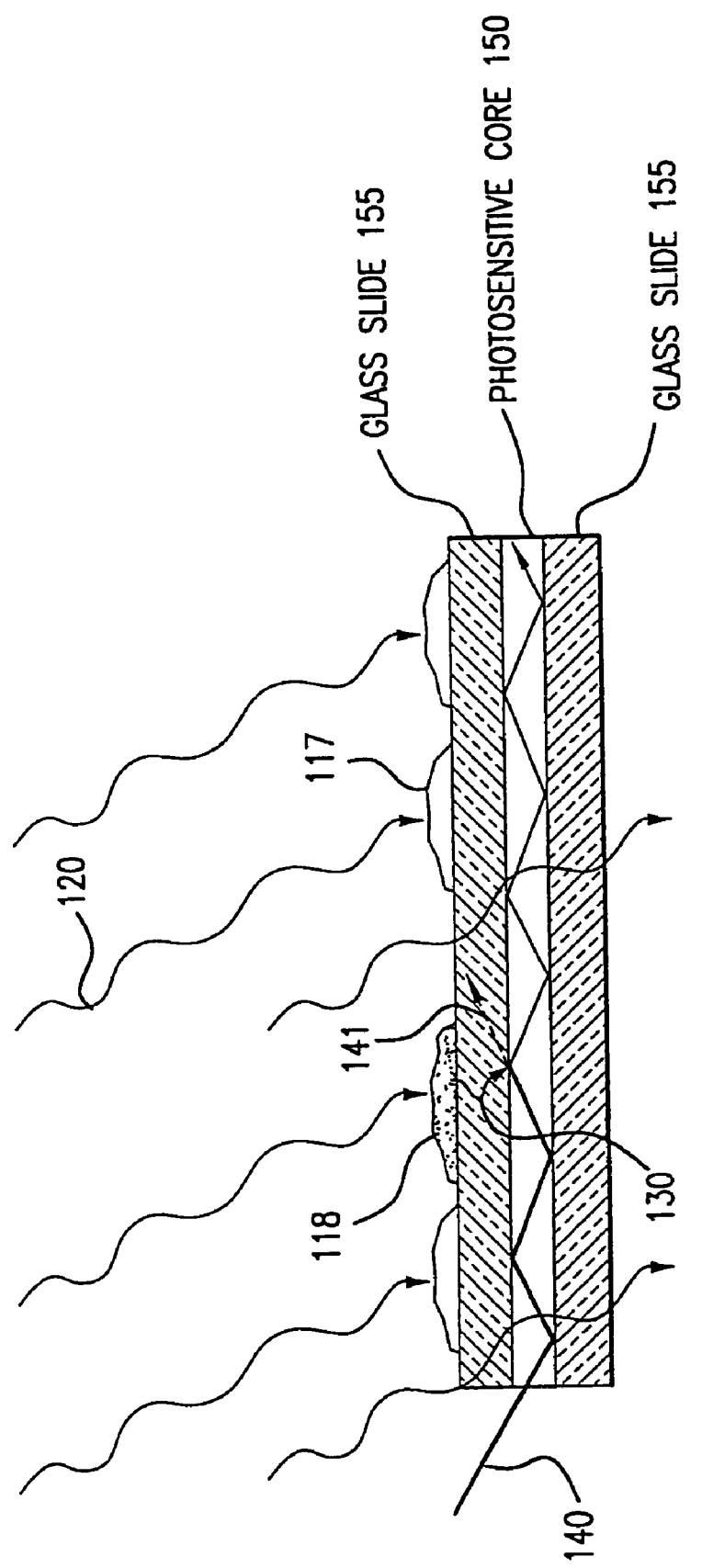

DEVICE AND METHOD FOR DETECTING AND LOCALIZING CELLS BY MEANS OF PHOTOSENSITIVE WAVEGUIDES

RELATED APPLICATIONS

This application is a continuation of U.S. patent application Ser. No. 10/182,210 filed Jul. 22, 2002, from which the benefit of priority is asserted and the specification of which is incorporated by reference in its entirety.

FIELD OF THE INVENTION

The present invention relates to the field of automated biological analysis systems and more specifically to automated cell detection systems employing waveguides having photosensitive components.

BACKGROUND

The automated detection of rare cells in a population of different cells is a challenging problem akin to finding the proverbial needle in the haystack. Examining cell sample using traditional microscopy would require unreasonable amounts of time and is susceptible to operator error. Furthermore, in some instances, for example, the detection of microbial cells in natural water ecosystems, the characteristics of the rare cells are not already known. In such situations optical microscopy based on image processing methods is the only viable alternative. A similar approach may be needed when the cells in question are known, but they are not identifiable through any other mechanism except with traditional microscopy and image processing, e.g. in the detection of cancer cells in pap-smears.

In cases where a specific characteristic of the rare cell can be identified and located through the generation of a distinct signal, detection methods other than image processing may be employed allowing for much faster detection in a very large initial population of cells. If, for example, a cell surface antibody specific to the cell in question can be bound to a fluorescing substance, the cell can be detected using fast methods such as fluorescence activated cell sorting (FACS). In such systems though the efficiency of detection is inversely proportional to the frequency of the cells in question.

U.S. Pat. No. 4,746,179 issued on May 24, 1988 to Dahne et al. describes the use of a waveguide in conjunction with a fluorescence signal generated by the sample to estimate the concentration of a soluble antigen. Dahne et al. passes an excitation signal through the waveguide that is immersed in, or in direct contact with, the sample solution. The leakage of the excitation signal from the waveguide reacts with the solution next to the waveguide and produces a fluorescence signal that is picked up by the waveguide and directed to and measured by a detector. The strength of the fluorescence signal will be proportional to the concentration of the sample in solution.

Citation or identification of any reference in this section or any section of this application shall not be construed that such reference is available as prior art to the present invention.

SUMMARY OF THE INVENTION

This present invention has for its objects devices, systems, and methods for identification of particles of interest in low concentrations and with high accuracy. Not only are particles of interest identified, but also their spatial position in a measurement region may be identified, permitting later verification by means of microscopic image processing. Although the present invention may be used to detect the presence and position of a wide range of particles, its primary application is to cell detection, wherein it improves on current methods of cell screening. In the following, but without limitation, the invention will be primarily described in its principal application.

The present invention achieves its objects by means of a novel and inventive combination of a two-dimensional (2D), photosensitive waveguide with a 2D scanning of the waveguide with the intersection of beams of radiation. In a photosensitive waveguide, the properties of guided radiation change in response to incident light. The photosensitive waveguides of the present invention are based on novel uses of nonlinear optical (NLO) effects that take place in certain substances. These effects result in changes of optical properties, such as index of refraction or absorptivity, in response to the intensity of the incident light. These substances can be various organic compounds e.g. conjugated dye molecules or special polymers. Such a compound may be used as a cladding for a cylindrical or a flat optical waveguide. A biological specimen containing various kinds of cells can be treated so that certain cells emit radiation to which the optical properties of the cladding ate responsive. If the cells are juxtaposed to the guide, it will affect the attributes of light radiation transferred by the waveguide. By monitoring the changes in the properties of the light transferred through the waveguide, one can detect the presence of the interesting cells.

This invention also provides for determining the location of interesting cells in a largely 2D measurement region by making use of the above detection principle. If two non-parallel beams are guided through a waveguide, both will have detectable changes if an emitting cell is in proximity to the intersection of the two beams. Thus, the presence and position of labeled cells can be determined by scanning the region of intersection of two non-parallel beams guided through the waveguide. In various alternatives, the waveguide may be moved or a beam of the fluorescence-inducing radiation can be scanned, or both.

In the following, a cell emitting radiation that controls a photosensitive waveguide will cause detectable changes in the properties of a light beam that is guided in proximity to the emitting cell. Typically, the necessary proximity is within one to three cell diameters.

In more detail, the present invention has several embodiments. In a first embodiment the invention includes a device for detecting the presence of one or more particles, wherein the particles emit controlling radiation and are placed in a measurement region, the device comprising: a photosensitive waveguide, wherein one or more properties of radiation guided through the waveguide are responsive to controlling radiation emitted by particles present in the measurement region, and a photo-detection system responsive to the one or more properties of the radiation guided through the photosensitive waveguide, wherein particles emitting controlling radiation in the measurement region cause changes in the one or more properties of the radiation guided through the waveguide which are detectable by the photo-detection system, whereby the system detects the presence of particles.

In a second embodiment the invention includes a system for detecting the presence and position of one or more cells which emit controlling radiation comprising: a measurement region in which the cells are affixed, a two-dimensional (2D)

photosensitive waveguide, wherein one or more properties of radiation guided through the waveguide are responsive to controlling radiation emitted by cells present in the measurement region, and a photo-detection system responsive to the one or more properties of a first beam of radiation and of a second beam of radiation, wherein the first and second beam are guided through the photosensitive waveguide in non-parallel directions, wherein cells emitting controlling radiation in the measurement region cause changes in the one or more properties of the first or the second beam of radiation when the beams guided through the waveguide in proximity to an emitting cell, the changed properties being detectable by the photo-detection system, whereby the system the presence and position of cells.

A first aspect of the second embodiment further includes means for moving the first and the second beam of radiation in non-parallel directions so that their region of intersection scans substantially all of the 2D photosensitive waveguide that is exposed to the measurement region, and a controller for providing control signals to the photo-detection system and to the means for moving. Further, the controller may include a memory, and a processor coupled to the memory and for causing the generation of the control signals, wherein the memory contains encoded program instructions for causing the processor to perform the steps of (i) generating control signals to cause the means for moving to move the first and the second beam of radiation so that their region of intersection scans substantially all of the measurement region, (ii) generating control signals to cause the photo-detection system to detect the changed properties of the beams, (iii) storing the positions of the beams when the photo-detection system detects changed properties, and (iv) computing the presence and position of cells from the stored positions.

In a third embodiment the invention includes a system for detecting the presence and position of one or more cells, wherein the cells are labeled to emit controlling radiation in response to incident activation radiation, the system comprising: a two-dimensional (2D) photosensitive waveguide, wherein one or more properties of radiation guided through the waveguide are responsive to controlling radiation emitted by cells present in the measurement region, and wherein the waveguide is planar and substantially disk shaped, and a measurement region in which the cells are affixed, means for rotating the disk-shaped 2D planar photosensitive waveguide together with the measurement region, a photo-detection system responsive to the one or more properties of a beam of radiation, wherein the beam is guided through the photosensitive waveguide along a diameter of the disk-shaped 2D planar photosensitive waveguide, and means for scanning a beam of activation radiation along the path of the beam guided though the waveguide, wherein the activation radiation causes the labeled cells to emit controlling radiation, wherein cells emitting controlling radiation in the measurement region in response to incident activation radiation cause changes in the one or more properties of the beam of radiation when the beam guided through the waveguide in proximity to an emitting cell, the changed properties being detectable by the photo-detection system, whereby the system the presence and position of cells.

A first aspect of the third embodiment further includes a controller for providing control signals to the means for rotating and to the means for scanning activation radiation, where the controller further includes a memory, and a processor coupled to the memory and for causing the generation of the control signals, wherein the memory contains encoded program instructions for causing the processor to perform the steps of (i) generating control signals to cause the means for rotating and the means for scanning so that the region of intersection of the beam guided through the waveguide and the activation beam scans substantially all of the measurement region, (ii) generating control signals to cause the photo-detection system to detect the changed properties of the beam guided through the waveguide, (iii) storing the angular position of the waveguide and the position of the beam of activation radiation when the photo-detection system detects changed properties, and (iv) computing the presence and position of cells from the stored positions.

In a fourth embodiment the invention includes a method for determining the presence and position of one or more cells which emit controlling radiation comprising: affixing the cell in a measurement region, wherein controlling radiation emitted in the measurement regions is incident on a two-dimensional (2D) photosensitive waveguide, and wherein one or more properties of radiation guided through the waveguide are responsive to controlling radiation emitted by cells present in the measurement region, guiding two or more beams of radiation through the 2D photosensitive waveguide at a series of positions so that the intersection of the beams scans substantially all of the 2D photosensitive waveguide illuminated by the measurement region, detecting the one or more properties of the beams guided through the waveguide, wherein presence and position of emitting cells is determined as the proximity of intersection of the beams when changed properties of the beams are detected.

In a fifth embodiment the invention also includes computer readable media comprising the encoded program instruction for the controllers of the invention.

In all embodiments it is preferable that the cells being detected are labeled with a fluorophore, and that the embodiment further comprise a source for activation radiation incident on the measurement region for stimulating the fluorophore to fluoresce. Then, this fluorescence is the controlling radiation.

BRIEF DESCRIPTION OF DRAWINGS

The present invention may be understood more fully by reference to the following detailed description of the preferred embodiment of the present invention, illustrative examples of specific embodiments of the invention and the appended figures in which:

FIG. 1A illustrates a side view of an embodiment of the present invention.

FIG. 1B illustrates a side view of another embodiment of the present invention.

DETAILED DESCRIPTION

Figure 2:
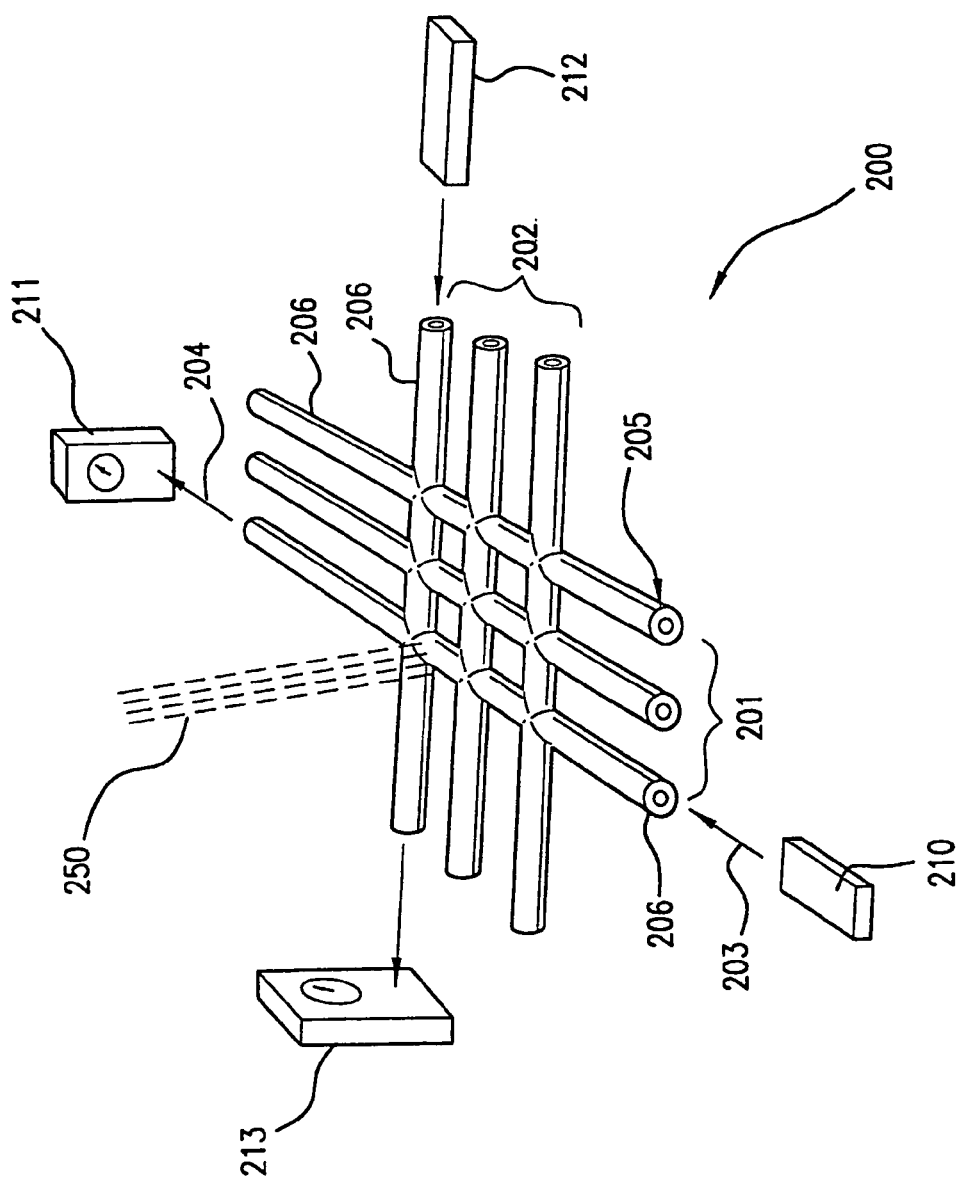
FIG. 2 illustrates a perspective view of another embodiment of the present invention.

The principles of the invention are described first with respect to FIGS. 1A–B. Following, several specific preferred embodiments of these principles are described along with the methods of use of these embodiments.

Principles of Cell Detection

FIG. 1A side view schematically illustrates one aspect of the principles of the present invention. Waveguide 100, illustrated in side view, includes a core 102 and a photosensitive cladding 104. The cladding and core materials are selected, as is well known in the art, to have relative indices of refraction at the wavelength of guided radiation 140 (illustrated here as propagating from left to right) and in view of the thickness of the core so that waveguide 100 functions correctly as a waveguide. In the following, waveguide function is primarily illustrated in the approximation in which light rays are contained in the core by total internal reflection at the core-cladding boundary. Also well known in the art are more accurate descriptions of waveguide function, such as by the equations of electromagnetism. The art of waveguides is widely described in numerous textbooks and publication; see, for example, Dorf ed., 1997, *The Electrical Engineering Handbook Second Edition,* CRC Press, Boca Raton, Fla. , chap 42 (page 1069–1095) and the reference cited therein. The term "light" is used herein to encompass not only visible electromagnetic radiation but also without limitation at least infra-red and ultra-violet radiation.

It is also important for the present invention that the core and cladding materials by further selected so that waveguide 100 is "photosensitive". By "photosensitive" is meant herein that the one or more aspects of the transmission of the light guided by a waveguide is responsive to controlling light ("light" is as understood above) incident on the waveguide at an angle such that it penetrates into the cladding, or the cladding and the core. Thus the incident angle of the controlling light is greater than the angle of total internal reflection at the interfaces to the cladding and the core which it must cross; preferably the incident angle is substantially orthogonal to the propagation direction of the guided light. For example, controlling light 130 penetrates the waveguide substantially orthogonal to guided light 140. Also, the controlling light may be otherwise different that the guided light, for example it may have a different wavelength. In a preferred embodiment;it is intensity of the guided light that is responsive to the controlling light; in other words, in this embodiment the transmissivity (or absorptivity) of the waveguide is responsive to the controlling light. In other embodiments, other optical properties of the guided light, such as its polarization (or propagation mode) may be responsive to the controlling light.

Waveguide photosensitivity is preferably achieved by further selecting either the cladding material, or the core material, or both materials to have one or more of their optical properties be responsive to the controlling radiation (i.e., be a photosensitive material). In the embodiment of FIG. 1A, it is the cladding material that is photosensitive. In this embodiment, selection of the core material is well known to those of ordinary skill in the art of optical waveguides and may include, without limitation, transparent organic polymers such as PMMA or polyacrylate, or transparent inorganic glasses. Selection of the cladding material will depend in part on the particular property responsive to the controlling light. Preferably, but without limitation, the refractive index of the cladding is responsive to the controlling light. Suitable cladding materials are referred to as nonlinear optical (NLO) materials and are described generally in, for example, *Chemical Reviews,* vol. 94, 1994. A review article providing various classes of NLO materials suitable for this invention is found in Moemer et al., 1994, Polymeric Photorefractive Materials, *Chemical Reviews* 94:127–156, and in Henk et al. 1998, SPIE Proc. vol. 2025B:292–297, both herein incorporated by reference for all purposes.

Operation of this embodiment, in which the index of refraction of the cladding is responsive to the controlling light, is readily explained using the internal-reflection approximation of waveguide function. Turning again to FIG. 1A, a light beam is confined to a waveguide by multiple total internal reflections of the light beam at the interface of the waveguide core 102 and the waveguide cladding 102, i.e., the material surrounding the core. Generally, cladding 104 has a thickness of at least several guided-light wavelengths, and may be a film on the core, or may be a surrounding gas or liquid, or may be a solid material adjacent to the core. Since the internal reflections at the core-cladding interface depend (in part) on the relative index of refraction of the core 102 and cladding 104, then if one or both indices change in an appropriate manner (to decrease the difference in the indices), the transmissivity of guided light beam 140 will decrease. Simply put, as the difference in the indices of refraction changes, for example, due to controlling light 130, some of the guided light will "leak" out of the waveguide and the transmissivity will decrease. (Conversely, if the difference in the indices increase, the transrnissivity may increase.) Changes in the intensity of the guided light can be detected and measured.

The photosensitive waveguides that produce detectable changes in guided-light intensity are exploited in the present invention by combining them with measurement regions. In operation, a measurement region contains particles (generally, localized materials) to be detected that emit controlling radiation, and is arranged with respect to the waveguide so that the emitted controlling radiation penetrates the cladding, or the core, or both, and causes a detectable change in the guided light. The measurement region can be separate and adjacent to a waveguide, as in FIG. 1A, or waveguide may form a part of the measurement regions, as in FIG. 1B. Since a principal application of this invention is to detection of biological cells, in the following the term "cells" is used for both cells in the biological sense and for localized particles in general.

In more detail, FIG. 1A illustrates measurement region 110 separate from but adjacent to photosensitive waveguide 100. Measurement region 110 comprises at least surface 116, which may be glass, plastic or other material, which is suitable for affixing sample 115 of cells to its surface. Affixing cells may be accomplished as is known in the art, for example, by chemical linking or with a surface treatment, by immunoabsorption on the surface, by coating with a retaining layer (not shown), by being embedded in transparent paraffin (not shown), or so forth. Sample 115, which preferably comprises biological cells and is affixed to surface 116 (such as a glass slide) comprises "common" cells 117 and "rare" cells 118. "Common" and "rare" are used herein to designate cells not of interest and cells of interest that are to be detected. These terms are not intended to limit the relative abundances of the designated cell types, although it is preferable for the rare cells to have a relative abundance of less the 25%, 10%, 5%, 1%, 0.5%, and less. (The methods of the present invention are more efficient and reliable at lower relative abundances of the cells of interest). For example, in a sample of maternal peripheral blood, maternal blood cells would be considered common cells not of interest while fetal cells in the sample would be considered rare cells of interest.

The cell sample is further prepared in many ways known in the biological and biochemical arts so that the rare cells emit controlling light, for example, by being labeled with a label that emits fluorescent light of a wavelength to which waveguide 100 is photosensitive. For example, the rare cells of interest may be labeled with an antibody to an extracellular or intracellular antigen not present in the common cells. This antibody may be directly conjugated to a suitable fluorophore, or the cells may be labeled with more fluorophore by one or more amplification steps, such as, by using anti-antibodies conjugated to the fluorophore. A suitable fluorophore is a compound which fluoresces with high quantum efficiency at a wavelength to which the waveguide is sensitive, and preferably is activated by light of a wavelength to which the waveguide is not sensitive.

Once the rare cells are suitably labeled and sample 115 placed in measurement region 110, it is illuminated with activation light 120, which causes the fluorophores labeling rare cell 118 to emit fluorescent light 130. Since common cells 117 are not so labeled, then do not emit the fluorescent light 130. The fluorescent light 130 emitted by the fluorophores is then absorbed by cladding 140, and the resulting changes in the index of refraction causes light leakage 141 in the region adjacent to rare cell 118 and a detectable decrease in the intensity of the guided light. Detection of decreased in guided-light intensity is hereinafter referred to as a detection event (or simple an "event"), and represents the detection of a rare labeled cell, A measurement region may also include certain optional elements. If the waveguide is also sensitive to the activation light of the fluorophore, a filter 112 may be positioned between the measurement regions and the cladding. The filter 112 may be a monochromatic filter or a narrow band filter that transmits fluorescent light but blocks activation light. A barrier layer (not shown) may optionally be positioned between the sample 115 and cladding 140 to prevent contamination of the waveguide 100 from the sample 115 and thereby allow reuse of the waveguide 115. In another embodiment, the waveguide is a single use disposable unit without a barrier layer.

A waveguide of this invention may also be photosensitive because one or more optical properties of the core are suitably photosensitive. For example, the absorptivity of the core may be sensitive to light of a first range of wavelengths while remaining transparent to light of a second range of wavelengths. FIG. 1B illustrates such embodiment of the present invention where the core 150 is composed of a photosensitive material normally transparent to the guided light 140 of the second range of wavelengths, but changes its transparency when it absorbs the fluorescent light 130 of the first range of wavelengths. A fluorophore labeling the rare cells is then chosen to emit fluorescent light in the first range of wavelengths. FIG. 1B also illustrates that the waveguide itself may be part of the measurement region. Here, the cladding 155 also serves as the sample support. In this case, a filter is not necessary, since the core is not sensitive to activation light 120.

In further embodiments, both the core and the cladding may be photosensitive. Optical properties other than the index of refraction or the absorptivity may be photosensitive. Additionally, photosensitive waveguides may be otherwise constructed, or may alter properties of the guided light other than its intensity.

Specific Two-dimensional Preferred Embodiments

FIGS. 1A–B, which depict a one-dimensional (1D) cross-section, illustrate that the presence of absence of one or more rare cells in a sample can be determined by detecting changes in guided light beam 140. Optionally, by detecting the degree of change, for example, the degree of attenuation, the number of rare cells may be approximately determined. But, in many cases, it is desirable to further examine rare cells that may be present, for example, by individual microscopic examination. To perform such examination, the position of rare cells must be determined.

The present invention determines the position of rare cells in a sample affixed to a surface by providing a two-dimensional (2D) photosensitive waveguide and by scanning the waveguide in both dimensions looking for simultaneous detection of the presence of rare cells. In certain alternatives, such 2D scanning may be achieved by scanning two non-parallel light beams. In other alternatives, 2D scanning may be achieved by scanning with one light beam in one direction while the waveguide itself is moved along a non-parallel direction. Finally, in both these embodiments, the activation light may uniformly illuminate the entire 2D waveguide while two intersecting light beams scan the illuminated region to detect an event and triangulation of the intersecting light beams to determine position. However, instead of scanning the light beams guided by the waveguide, in further alternative, the activation light itself may be focused onto a small region, a spot, on the waveguide and scanned over the entire waveguide using a single light beam tracking the movement of the activation light to detect an event and the position of the activation light spot to determine position of the event. In the following specific preferred embodiments of these alternatives are described.

FIG. 2 illustrates a perspective view of one embodiment of a photosensitive 2D waveguide scanned by two non-parallel light beams. The waveguide 200 comprises a first set of parallel optical fibers 201 fused to a second set of parallel optical fibers 202 oriented perpendicular to the first set of fibers. The fused mesh of fibers is coated with cladding material 205 to form the waveguide 200. The core and cladding materials are selected to form a photosensitive waveguide, as previously described. A first light source 210 is positioned to propagate guided light 203 along each fiber of the first set of fibers, and a first detector 211 is positioned to measure the transmitted light 204 guided through each of the first set of fibers 201. Both the first light source 210 and first detector 211 may be mounted on a single support that sequentially positions the source and detector to measure light guided through each of the fibers in the first set of fibers 201. Alternatively, the light source may be an array of light sources, such as LEDs, with each LED positioned in front of a single fiber 206, and the first detector may be an array of detectors, such as CCDs, oriented at the end of each fiber and facing the light source. Such an approach provides for more rapid detection and localization because it eliminates the mechanical scanning. Similarly, a second light source 212 and second detector 213 are disposed to transmit and measure the transmitted light through each of the fibers in the second set of fibers 202. The fibers may have diameters between 1 and 50 micrometers, preferably between 10 and 1 micrometers, and most preferably between 5 and 2 micrometers in diameter. The sample is placed on the waveguide 200 (which forms part of the measurement region) and illuminated by an activation light. Alternatively, the measurement region may include a separate sample support, and optionally an activation light filter. The activation light causes the rare cells to emit fluorescent radiation 250 that changes, for example, the index of refraction of the cladding (or the absorptivity of the core) at an intersection of a fiber from the first set of fibers and a fiber from the second set of fibers, thereby reducing the transmission of light through each of the affected fibers. Coordinate of the rare cell is determined by calculating the distance to the affected first fiber along the first set of fibers and the distance to the affected second fiber along the second set of fibers.

Figure 3:
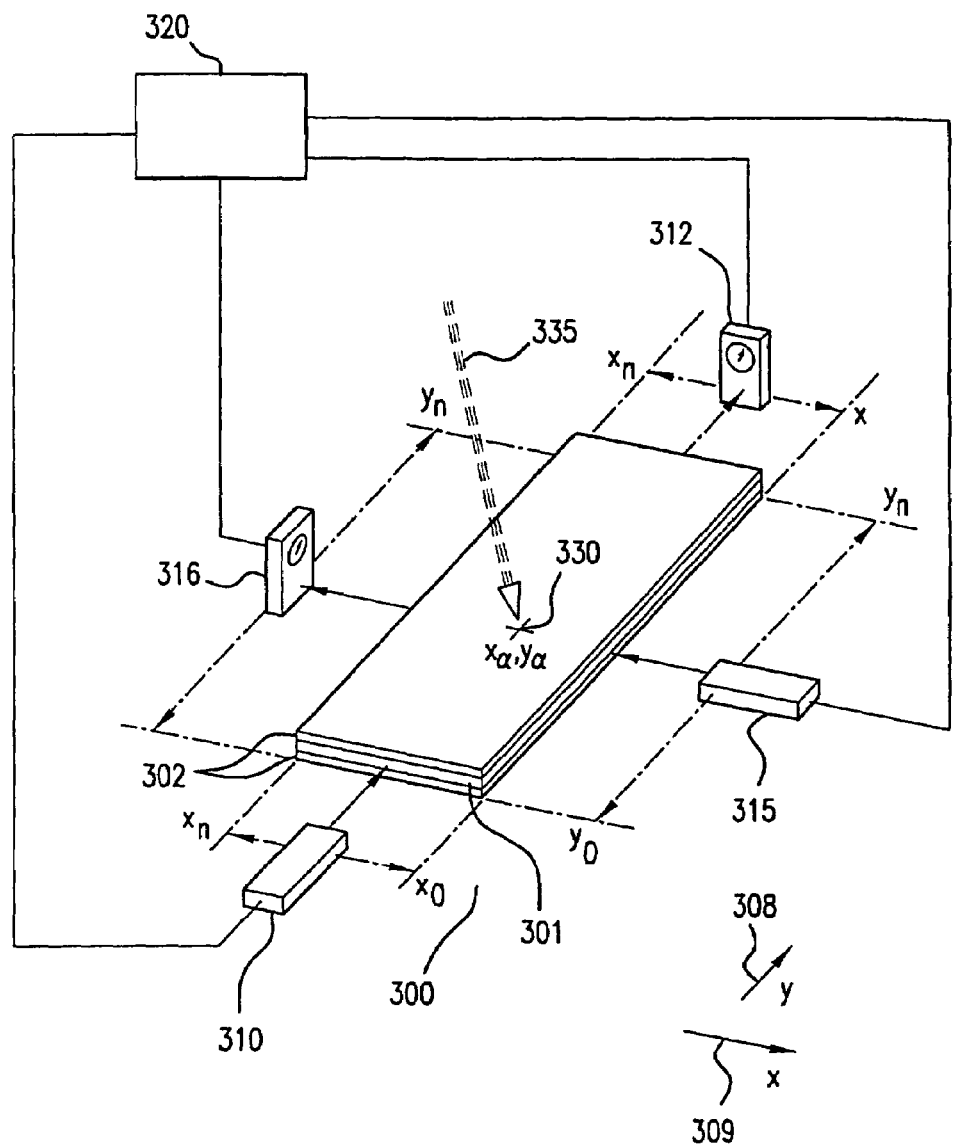
FIG. 3 illustrates a perspective view of another embodiment of the present invention.

FIG. 3 illustrates a perspective view of an embodiment similar to that of FIG. 2, but having a 2D waveguide different from the previously-described optical-fiber mesh. The 2D waveguide of FIG. 3 is planar, constructed from planar core sheet 301 sandwiched between photosensitive cladding sheets 302. These sheets may have thicknesses of between 1 and 50 micrometers, preferably between 10 and 1 micrometers, and most preferably between 5 and 2 micrometers. Their materials are selected so that planar waveguide 300 is appropriately photosensitive, and may be mounted on a substrate for physical support. A first photo-detector comprises a first light source 310 oriented to transmit light in the y-direction 308 and a first detector 312 oriented to measure light transmission in the y-direction 308. Both the first light source and the first detector are capable of translation in the x-direction 309. A second photo-detector comprises a second light source 315 oriented to transmit light in the x-direction 309 and a second detector 316 oriented to measure light transmission in the x-direction 309. Both the second light source 315 and second detector 316 are capable of translation in the y-direction 308. These photo-detectors may be scanned in other geometrically-complete patterns. The light sources are such that the light beams have limited lateral spread, for example the source may include collimating optics.

A preferably programmable controller 320 controls means for translating (not shown) the first photo-detector in the x-direction 309, means for translating (not shown) the second photo-detector in the y-direction 308, and stores the measured values from the first and second detectors detects. The controller further detects the presence of rare cells in beams from the light sources and performs a geometric calculation to locate each rare cell in the sample. The means for translating the light sources and detectors may be standard controllable laboratory devices as known in the art.

Specifically, the controller may first perform a calibration sweep with no sample on the planar waveguide. The controller performs a first photo-detector calibration by turning on the first light source, measuring the transmitted light with the first detector and storing the transmitted light values as the controller translates the first light source and first detector in the x-direction. The controller then performs a second photo-detector calibration by turning on the second light source, measuring the transmitted light with the second detector and storing the transmitted light values as the controller translates the second light source and second detector in the y-direction. A sample is placed in a measurement region adjacent to or on the planar waveguide and illuminated with an activation light source that causes the labeled rare cells to fluoresce, and to thereby change the index of refraction of the cladding in the vicinity of the fluorescing cell. The controller 320 performs a first photo-detector scan by measuring the transmitted light and comparing the value of the transmitted light to the calibration value for the position corresponding to the present location of the first detector 312 along the x-direction 309. If the difference between the two values is significant, for example, is greater than a preset threshold value, a rare-cell-detection event is declared by the controller and the distance along the x-direction is stored by the controller 320. The controller 320 performs a second photo-detector scan by measuring the transmitted light and comparing the value of the transmitted light to the calibration value for the position corresponding to the present location of the second detector 312 along the y-direction 308. If the difference between the two values are greater than a preset threshold value, the distance along the y-direction is stored by the controller 320. If the sample contains more many rare cells, the computed location may be ambiguous. This ambiguity is minimized by lowering the relative abundance of rare cells. It may be overcome by techniques such as partially rotating the 2D waveguide and again performing the scans, where only rare cell locations found in both waveguide orientations are true rare-cell locations.

A further complication arises when two or more events align on a single light beam. The controller 320 will not be able to distinguish between a single event and a plurality of events unless the reduction in transmission per event is known. The relation between transmission and number of events can be roughly estimated during a calibration step where a calibration standard is used to determine the transmission through the waveguide as a function of events. The calibration standard contains markers-of known size and location that emit fluorescent radiation when illuminated by the activation light. As the two photo-detectors scan the waveguide, the controller correlates the measured transmission values to the expected number of events based on the geometry of the calibration standard.

The ambiguities described above may be eliminated by illuminating only a portion of the waveguide with the activation light. The illuminated region, hereinafter referred to as the illumination spot is then scanned over the entire waveguide. Only rare cells illuminated by the illumination spot will emit fluorescent radiation that affects the photosensitive cladding and thereby affects the transmission of light through the waveguide. The controller 320 controls the movement of the illumination spot and is capable of determining the position of the illumination spot on the waveguide using techniques known to one of ordinary skill in the electromechanical control art. Referring to FIG. 3, an event 330 is shown having a location at $(X_a, Y_a)$. The event 330 emits fluorescent radiation that is partially absorbed by the photosensitive cladding in the vicinity of the event and causes the. cladding to change its refractive properties such that the transmission of light through the waveguide that passes under the event 330 is altered. If the sample is uniformly illuminated, two photo-detectors are required to locate the event 330 because the event 330 could be from any location on the waveguide. However, if the sample is illuminated by a focused illumination beam 335, only rare cells located in the illumination spot will emit the fluorescent radiation that alters the cladding properties and affects the transmission of light through the waveguide. The controller 320 has means to determine the location of the illumination spot on the waveguide and determines the position of an event. Therefore, only one photo-detector is required to provide for the detection of the event 330.

Figure 4A:
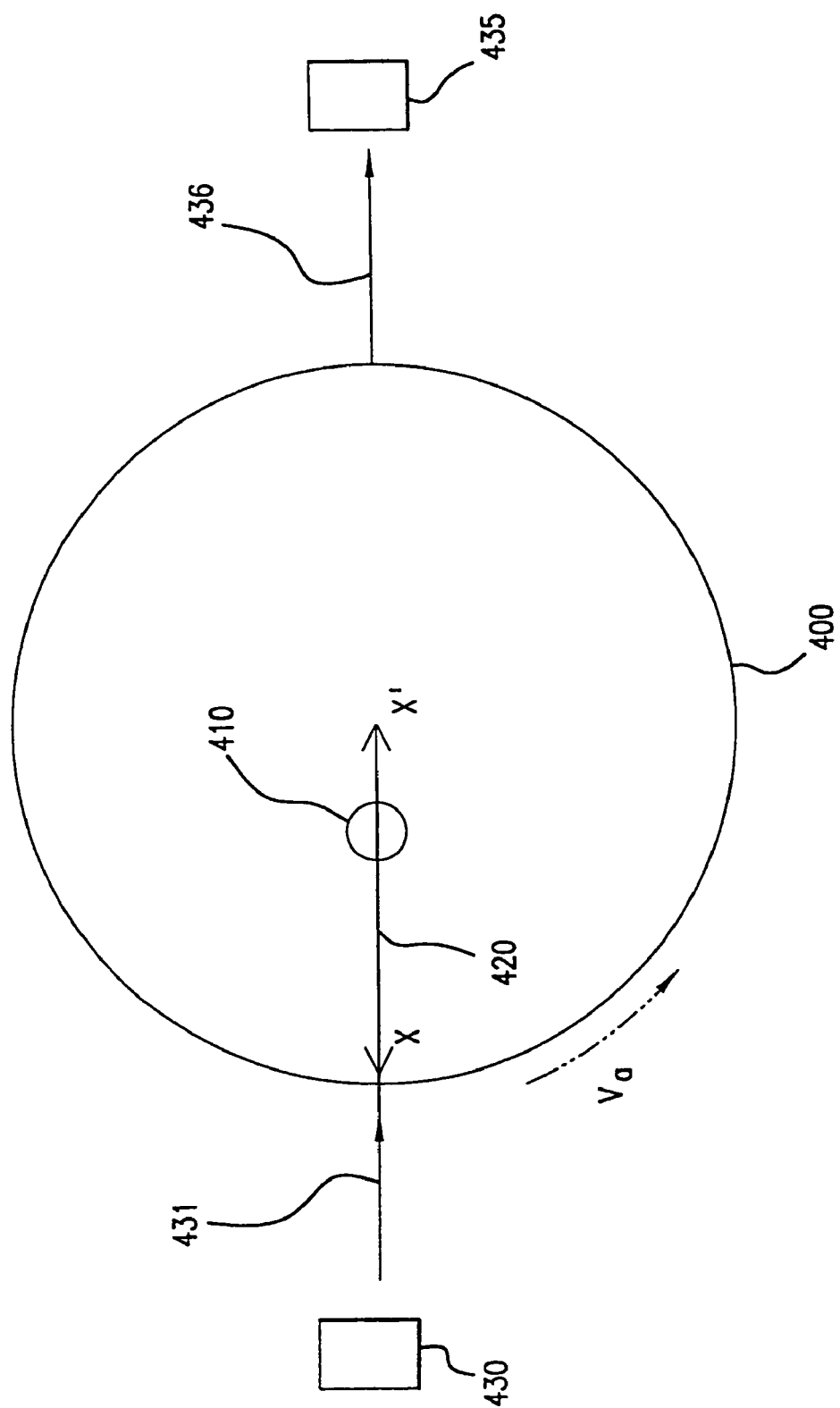
FIG. 4A illustrates a top view of another embodiment of the present invention.
Figure 4B:
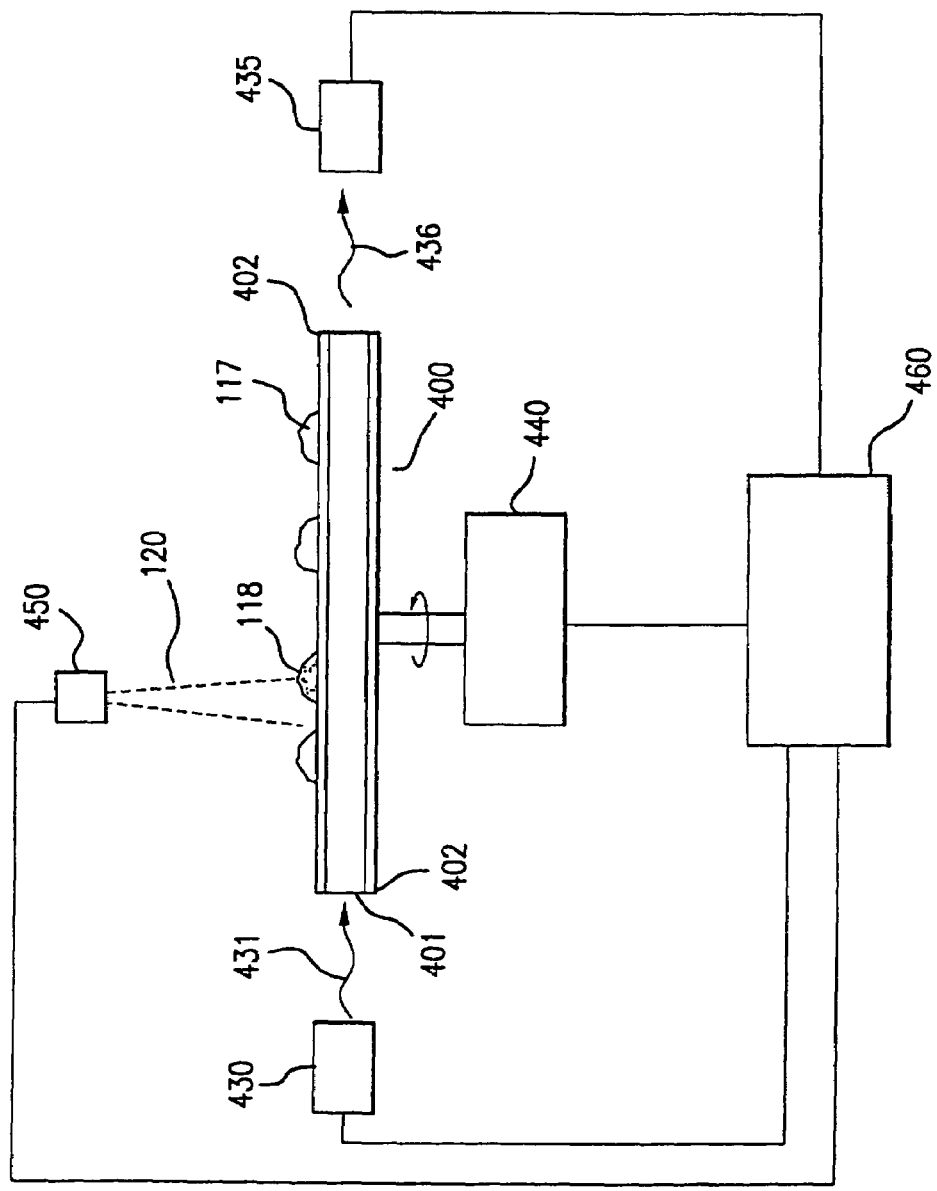
FIG. 4B illustrates a side view of the embodiment shown in FIG. 4A.

FIG. 4A (depicting a top view) and FIG. 4B (depicting a side view) together illustrate an embodiment of the present invention in which a 2D photosensitive waveguide is moved while being a localized region of activation light is scanned in an orthogonal direction. In this embodiment, planar waveguide 400, comprising planar core sheet 401 sandwiched between photosensitive cladding sheets 402, is substantially circular and is mounted for rotation on support 440. This planar waveguide may be constructed as in the embodiment of FIG. 3, in particular, including a supporting substrate. However, instead of illuminating the entire sample region with activation light as in the previously-described embodiments, only a small portion 410 of the region is illuminated by the activation light 120. Preferably, this portion is of the sized in conformance with the desired accuracy of rare-cell position determination. Activation light source 450 (with necessary optics) is then translated in the radial direction of the rotating disk waveguide along path XX' 420. Light source 430 directs light beam 431 (of limited lateral dispersion) through waveguide 400 along a path coincident with path XX' 420. A detector 435 disposed opposite the light source 430 and oriented to face the light source measures the transmitted light 436 through the waveguide 400. Programmable controller 460 controls light source 430, activation light source 450, means for moving (not shown) the activation light source 450 along path XX' 420, means for rotating support 440.

Controller 460 also calculates positions of rare cells in the sample. It receives, processes, and stores the position and rotation angle of the waveguide 400 and the signal from light detector 435. Rare-cell position is then routinely determined from the angle of the waveguide and the position of activation light when the light detector observes an event.

Methods of the Invention

The presence and position of rare cells in an appropriately prepared sample placed in a measurement region of the devices of the present invention are preferably automatically determined. As described with respect to the previous embodiments, a preferably-programmable controller provides control signals to light sources, light detectors, and the mechanical means for moving the light sources, detectors, and perhaps also the waveguides. A preferred controller includes a microprocessor and RAM memory for holding software instructions to cause the microprocessor to carry out the methods of this invention. A preferred controller also includes interfaces to provide control signals under program control and user interfaces for control and reporting of results. Software instructions for performing this invention's methods may be loaded into the controller from computer readable media of convenient types, such as magnetic or optical discs, or may be permanently stored in a ROM memory.

Figure 5:
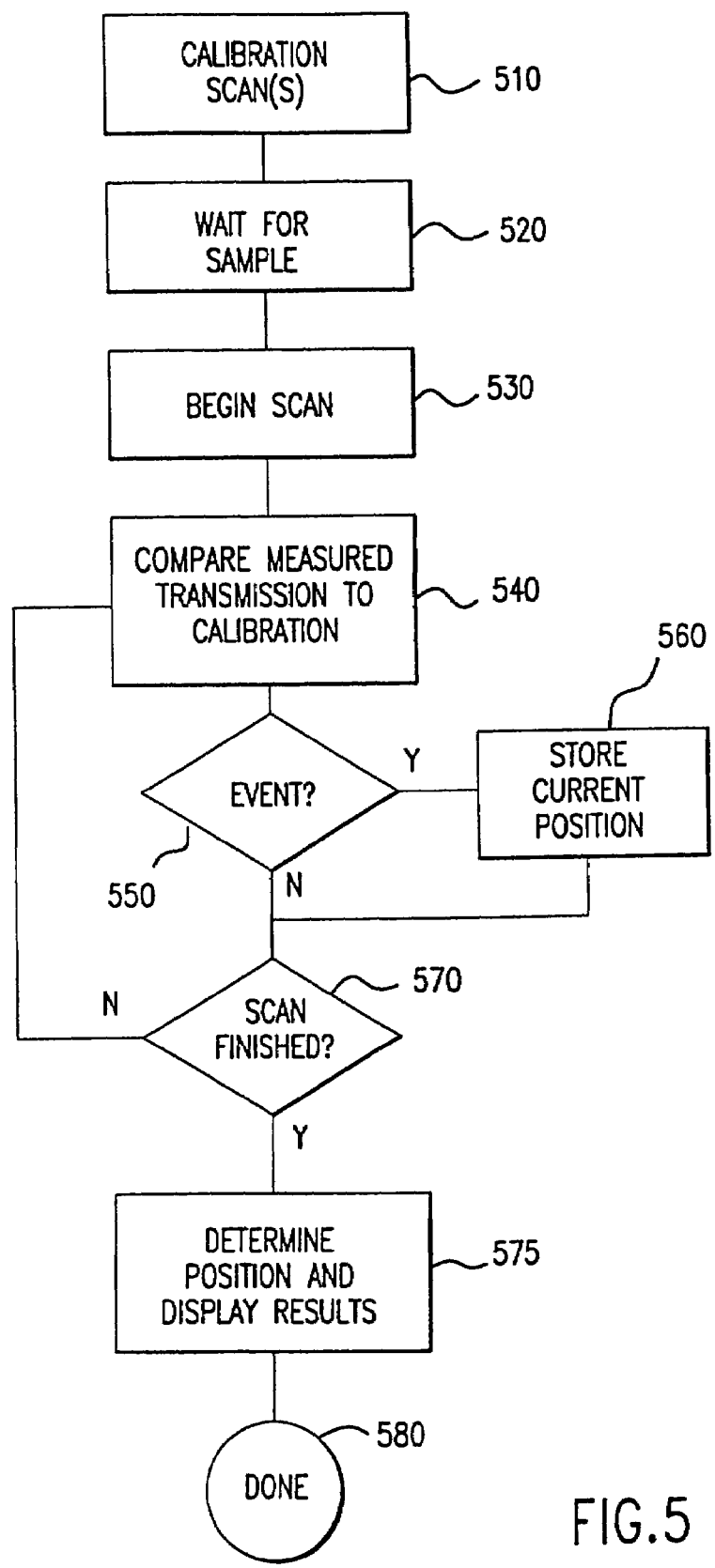
FIG. 5 illustrates a flow diagram for the invention.

A preferred embodiment of the methods of this invention are described with reference to FIG. 5. Although FIG. 5 primarily illustrates controller operation for the embodiment shown in FIG. 4A, it is largely also applicable to the embodiments of FIGS. 2 and 3 with routine modification. The controller first performs a calibration scan 510 by measuring and storing the transmitted light values as a function of rotation angle of the disk without a sample while rotating the disk a full 360 degrees. For the device of FIG. 2, the controller performs two calibration scans for each of the light source-detector combination. The controller then waits 520 until an appropriately prepared and labeled sample is placed in the measurement region, which may be adjacent to or on the planar disk waveguide.

The controller scanning the sample in step 530 by moving the activation light source to one end of the path XX', turning on the activation light 450 and light source 430, rotating the support 440, and translating the activation light 450 along path XX' 420. If a tagged cell is within the illuminated area, the activation light will cause the marker fluoresce. The fluorescent radiation will be partially absorbed by the photosensitive cladding causing the cladding to change its refractive index and thereby change the transmitted light through the waveguide. The controller compares the measured value of transmitted light from the detector to the calibrated value for the current rotation angle in 540. If the difference between the two values is significant, for example, by being greater than a preset threshold value, an event is declared indicating the detection of a rare cell 550. The controller stores the current rotation angle of the disk and the location of the activation light source in 560. The controller checks if the whole disk has been scanned in 570. If the whole disk has not finished scanning, the controller jumps to 540 and continues to rotate the disk, translate the activation light source, and compare the measured transmission to the calibrated value.

If the whole disk has been scanned, the controller, in step 575, determines the location of events, that is of rare cells, from the stored rotation angles and the corresponding stored activation-light-source location along the XX' path. These results are then displayed or reported to a user, and the controller exits.

The present invention includes other implementations of these methods that will be apparent to one of skill in the art. For example, event position can be determined in step 560.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A photosensitive waveguide for locating and identifying a fluorophore-labeled cell by scanning light microscopy using two non-parallel light beams, the photosensitive waveguide comprising:
   a first set of parallel optical polymer fibers fused in perpendicular orientation to a second set of parallel optical polymer fibers, each fiber being composed of a core enclosed by a cladding;
   wherein a first light source is positioned to propagate guided light along each fiber of the first set of fibers and first light detector is positioned to measure the transmitted light guided through each of the first set of fibers; and a second light source is positioned to propagate guided light along each fiber of the second set of fibers and second light detector is positioned to measure the transmitted light guided through each of the second set of fibers;
   wherein the fiber core and cladding comprise a photosensitive substance for guiding light beams to and from a light emitting fluorophore-labeled cell; the light beams being detected at positions determining the cell location and identity in a measurement area.

2. The waveguide of claim 1, wherein the fiber core and the cladding surrounding the core comprise an optical property selected from relative refractive indices.

3. The waveguide of claim 1, wherein the fiber core is selected from a material responsive to guided light radiation in said first and said second set of fibers.

4. The waveguide of claim 1, wherein the fiber core has an absorptivity responsive to a controlling light radiation emitted from one or more than one cell, and wherein the controlling light radiation decreases the intensity of the radiation guided through the waveguide by causing light to be absorbed in the core.

5. The waveguide of claim 1, wherein the optical polymer fibers are selected from an organic matter or an inorganic matter.

6. The waveguide of claim 1, wherein a controlling radiation is emitted from the fluorophore-labeled cell in response to incident activation radiation in the measurement area.

7. The waveguide of claim 6, wherein the activation radiation stimulates the fluorescence of the fluorophore-label.

8. The waveguide of claim 1, wherein the fibers comprise a substantially cylindrical shape.

9. The waveguide of claim 1, wherein the measurement area comprises cells that are affixed to a support.

10. The waveguide of claim 1, comprising a two-dimensional (2D) aspect in the measurement area.

11. The waveguide of claim 1, wherein the 2D photosensitive waveguide is formed by a mesh of intersecting first and second sets of parallel optical fibers.

12. The waveguide of claim 1, wherein at least one of the cladding layers has an index of refraction responsive to a controlling radiation so as to decrease the intensity of the radiation guided through the waveguide by causing light to leak from the waveguide through the cladding in proximity to the controlling radiation.

13. The waveguide of claim 12, wherein the core layer has an absorptivity responsive to the controlling radiation, and wherein the controlling radiation decreases the intensity of the radiation guided through the waveguide by causing light to be absorbed in the core layer in proximity to the controlling radiation.

14. The waveguide of claim 1, wherein the positions of the first and second light sources are determined by a computer readable media in accord with an encoded program capable of locating and identifying the fluorophore-labeled cell in the measurement area.

15. The waveguide of claim 1, wherein the light source comprises an array of light sources.

16. The waveguide of claim 15, wherein the array of light sources comprises an LED where each LED is positioned in front of a single fiber.

17. The waveguide of claim 1, wherein the detector comprises an array of detectors selected from suitable CCDs, oriented at each fiber end and facing the light source.

* * * * *